(12) United States Patent
Ehr et al.

(10) Patent No.: US 7,442,203 B2
(45) Date of Patent: *Oct. 28, 2008

(54) STENT CONFIGURATIONS

(75) Inventors: Timothy G. J. Ehr, Elk River, MN (US); Graig L. Kveen, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 563 days.

This patent is subject to a terminal disclaimer.

(21) Appl. No.: 10/321,089

(22) Filed: Dec. 17, 2002

(65) Prior Publication Data

US 2003/0120335 A1    Jun. 26, 2003

Related U.S. Application Data

(63) Continuation of application No. 10/164,989, filed on Jun. 6, 2002, now abandoned, which is a continuation of application No. 09/707,447, filed on Nov. 7, 2000, now Pat. No. 6,471,720, which is a continuation of application No. 09/151,053, filed on Sep. 10, 1998, now Pat. No. 6,193,744.

(51) Int. Cl.
*A61F 2/06*    (2006.01)
(52) U.S. Cl. .................................... 623/1.17
(58) Field of Classification Search ......... 623/1.1–1.22, 623/1.3–1.34
See application file for complete search history.

(56) References Cited

U.S. PATENT DOCUMENTS

| 5,102,417 A | 4/1992 | Palmaz ........................ 606/195 |
| 5,314,472 A | 5/1994 | Fontaine ....................... 623/12 |
| 5,449,373 A | 9/1995 | Pinchasik et al. ........... 606/198 |
| 5,507,767 A | 4/1996 | Maeda et al. ................. 623/12 |
| 5,593,442 A | 1/1997 | Klein .......................... 606/198 |
| 5,613,981 A | 3/1997 | Boyle et al. ................. 606/195 |
| 5,653,727 A | 8/1997 | Wiktor ........................ 606/198 |
| 5,733,303 A | 3/1998 | Israel et al. ................. 606/198 |
| 5,735,871 A | 4/1998 | Sgro ............................. 623/1 |
| 5,735,893 A | 4/1998 | Lau et al. ....................... 623/1 |
| 5,755,781 A | 5/1998 | Jayaraman |
| 5,759,192 A | 6/1998 | Saunders .................... 606/194 |

(Continued)

FOREIGN PATENT DOCUMENTS

DE    29701 758 U1    3/1997

(Continued)

OTHER PUBLICATIONS

U.S. Appl. No. 60/073,412, filed Feb. 2, 1998, Jang.

(Continued)

*Primary Examiner*—Todd E. Manahan
*Assistant Examiner*—Elizabeth Houston
(74) *Attorney, Agent, or Firm*—Vidas, Arrett & Steinkraus, P.A.

(57) ABSTRACT

Improved stent configurations exhibiting limited recoil, resistance to compression and improved longitudinal flexibility are disclosed. The stent comprised of a plurality of annular elements aligned to form a cylindrical stent body. The annular elements are comprised of a plurality of open, generally boomerang-shaped segments interconnected top-to-bottom around each of the annular elements. Adjacent annular elements are interconnected by interconnecting element.

19 Claims, 9 Drawing Sheets

U.S. PATENT DOCUMENTS

| | | | | |
|---|---|---|---|---|
| 5,776,161 | A | 7/1998 | Globerman | 606/194 |
| 5,807,404 | A | 9/1998 | Richter | 623/1 |
| 5,810,872 | A | 9/1998 | Kanesaka et al. | 606/198 |
| 5,824,043 | A | 10/1998 | Cottone, Jr. | 623/1 |
| 5,827,321 | A | 10/1998 | Roubin et al. | 606/195 |
| 5,855,600 | A | 1/1999 | Alt | 623/1 |
| 5,868,781 | A | 2/1999 | Killion | 606/198 |
| 5,876,449 | A | 3/1999 | Starck et al. | 623/12 |
| 5,895,406 | A | 4/1999 | Gray et al. | 606/198 |
| 5,897,588 | A | 4/1999 | Hull et al. | 623/1 |
| 5,902,332 | A | 5/1999 | Schatz | 623/1 |
| 5,911,754 | A | 6/1999 | Kanesaka et al. | 623/1 |
| 5,922,021 | A | 7/1999 | Jang | 623/1 |
| 5,928,280 | A * | 7/1999 | Hansen et al. | 623/1.15 |
| 5,938,682 | A | 8/1999 | Hojeibane et al. | 606/198 |
| 5,948,016 | A | 9/1999 | Jang | 623/1 |
| 5,954,743 | A | 9/1999 | Jang | 606/198 |
| 5,980,553 | A | 11/1999 | Gray et al. | 606/198 |
| 6,017,365 | A | 1/2000 | Von Oepen | 623/1 |
| 6,033,433 | A | 3/2000 | Ehr et al. | 623/1 |
| 6,066,169 | A | 5/2000 | McGuinness | 623/1.16 |
| 6,068,656 | A | 5/2000 | Von Oepen | 623/1.17 |
| 6,099,561 | A | 8/2000 | Alt | 623/44 |
| 6,113,627 | A | 9/2000 | Jang | 623/1 |
| 6,123,721 | A | 9/2000 | Jang | 623/1 |
| 6,146,417 | A | 11/2000 | Ischinger | 623/1.15 |
| 6,190,403 | B1 | 2/2001 | Fischell et al. | 623/1 |
| 6,193,744 | B1 * | 2/2001 | Ehr et al. | 623/1.16 |
| 6,193,747 | B1 * | 2/2001 | von Oepen | 623/1.15 |
| 6,200,334 | B1 | 3/2001 | Jang | 623/1.1 |
| 6,231,598 | B1 | 5/2001 | Berry et al. | 623/1.15 |
| 6,235,053 | B1 | 5/2001 | Jang | 623/1.15 |
| 6,261,319 | B1 | 7/2001 | Kveen et al. | 623/1.15 |
| 6,331,189 | B1 | 12/2001 | Wolinsky et al. | 623/1.15 |
| 6,352,552 | B1 | 3/2002 | Levinson et al. | 623/1.15 |
| 6,355,057 | B1 | 3/2002 | DeMarais et al. | 623/1.15 |
| 6,355,059 | B1 | 3/2002 | Richter et al. | 623/1.17 |
| 6,398,805 | B1 | 6/2002 | Alt | 623/1.15 |
| 6,409,761 | B1 | 6/2002 | Jang | 623/6.12 |
| 6,416,538 | B1 | 7/2002 | Ley et al. | 623/1.15 |
| 6,423,090 | B1 | 7/2002 | Hancock | 623/1.15 |
| 6,432,133 | B1 | 8/2002 | Lau et al. | 623/1.15 |
| 6,443,982 | B1 | 9/2002 | Israel et al. | 623/1.17 |
| 6,451,049 | B2 | 9/2002 | Vallana et al. | 623/1.15 |
| 6,461,380 | B1 | 10/2002 | Cox | 623/1.17 |
| 6,461,381 | B2 | 10/2002 | Israel et al. | 623/1.17 |
| 6,464,720 | B2 | 10/2002 | Boatman et al. | 623/1.15 |
| 6,464,722 | B2 | 10/2002 | Israel et al. | 623/1.17 |
| 6,468,302 | B2 | 10/2002 | Cox et al. | 623/1.15 |
| 6,471,720 | B1 | 10/2002 | Ehr et al. | 623/1.15 |
| 6,475,236 | B1 | 11/2002 | Roubin et al. | 623/1.15 |
| 6,478,816 | B1 | 11/2002 | Kveen et al. | 623/1.15 |
| 6,485,508 | B1 | 11/2002 | McGuinness | 623/1.15 |
| 6,497,723 | B1 | 12/2002 | Starck et al. | 623/1.15 |
| 2003/0093144 | A1 | 5/2003 | Jang | 623/1.15 |

FOREIGN PATENT DOCUMENTS

| | | | |
|---|---|---|---|
| DE | 297 02 671 U1 | | 4/1997 |
| DE | 19834956 | | 5/1999 |
| EP | 734698 | | 10/1996 |
| WO | 97/09945 | | 3/1997 |
| WO | 97/14375 | | 4/1997 |
| WO | 97/26840 | | 7/1997 |
| WO | WO-98/07386 | * | 8/1997 |
| WO | 97/32543 | | 9/1997 |
| WO | 97/40780 | | 11/1997 |
| WO | 98/07386 | | 2/1998 |
| WO | 98/32412 | | 7/1998 |
| WO | 98/40035 | | 9/1998 |
| WO | 98/44871 | | 10/1998 |
| WO | 99/39660 | | 3/1999 |
| WO | 99/17680 | | 4/1999 |

OTHER PUBLICATIONS

U.S. Appl. No. 09/839,287, filed Apr. 20, 2001, Jang.
U.S. Appl. No. 09/707,447, filed Nov. 7, 2000, Ehr et al.
U.S. Appl. No. 09/151,053, filed Sep. 10, 1998, Ehr et al.

* cited by examiner

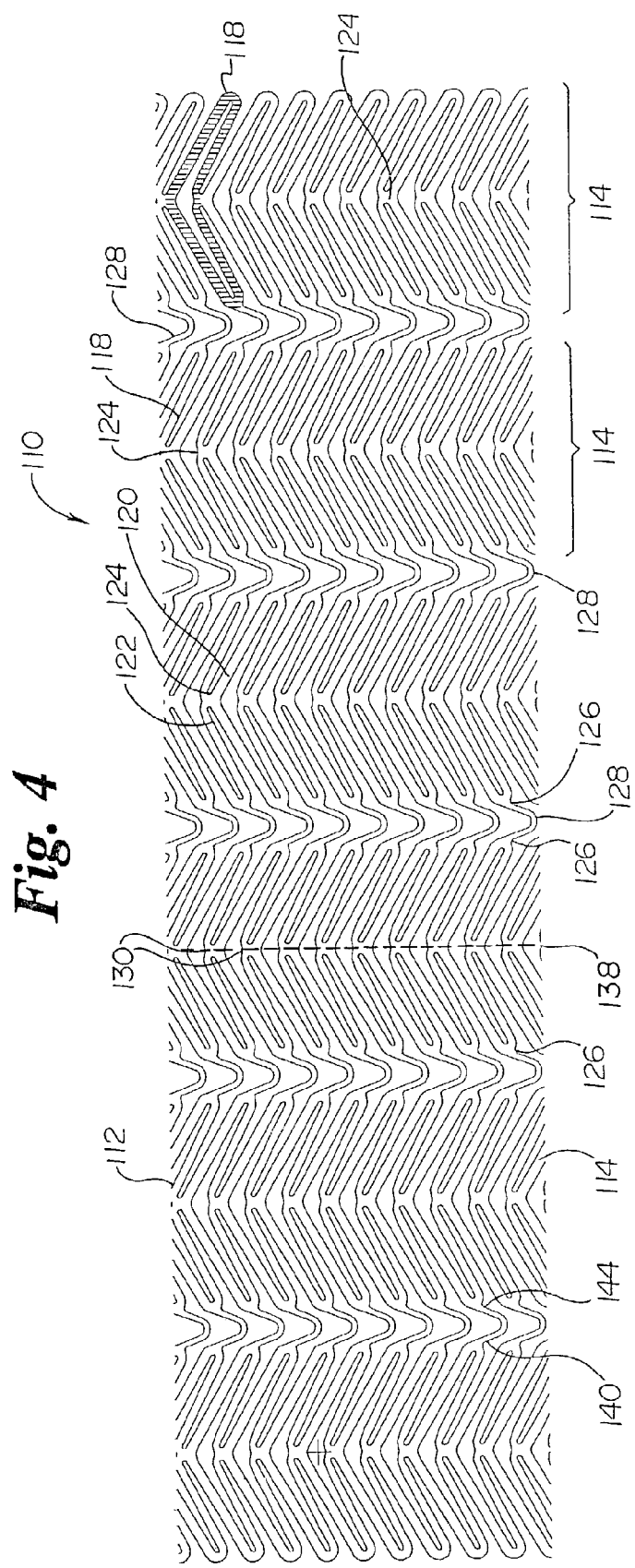

STENT CONFIGURATIONS

CROSS REFERENCE TO RELATED APPLICATIONS

This Application is a continuation of U.S. application Ser. No. 10/164,989, filed Jun. 6, 2002, now abandoned; which is a continuation of U.S. application Ser. No. 09/707,447, filed Nov. 7, 2000, now U.S. Pat. No. 6,471,720; which is a continuation of U.S. application Ser. No. 09/151,053, filed Sep. 10, 1998, now U.S. Pat. No. 6,193,744, the contents of all of which are incorporated herein in their entirety by reference.

BACKGROUND OF THE INVENTION

1. Field of the Invention

This invention relates to stents of improved configuration.

2. Brief Description of the Prior Art

Stents are radially expandable endoprosthesis which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

In the past, stents have been generally tubular but have been composed of many configurations and have been made of many materials, including metals and plastic. Ordinary metals such as stainless steel have been used as have shape memory metals such as Nitinol and the like. Stents have also been made of biodegradable plastic materials. Such stents have been formed from wire, tube stock, etc. Some stents are self-expanding and some are expanded by an interior radial force.

SUMMARY OF THE INVENTION

This invention provides new configurations of the segments making up stents which may be adapted to all of the various types of prior art stents described above and/or known previously in the art. There are numerous advantages to the new configurations. For example, the configurations of the invention limit recoil and add resistance to compression for an expanded stent, among other things. Also, the stents of this invention are longitudinally flexible.

The inventive stents comprise a plurality of annular elements aligned to form a cylindrical stent body. Each annular element, in turn, is comprised of a plurality of open, generally boomerang-shaped segments. The segments are interconnected top-to-bottom around each of the annular elements. Adjacent annular elements are interconnected by one or more interconnecting elements. Each interconnecting element extends from an end of a boomerang-shaped segment in one annular element to an end of a boomerang-shaped segment in an adjacent annular element. In a preferred embodiment an interconnecting element extends from each boomerang-shaped segment in an annular element to a neighboring boomerang-shaped segment in an adjacent annular element.

Interconnecting elements joining adjacent annular elements are desirably U-shaped or zig-zag shaped, although other curvilinear and rectilinear interconnecting elements may also be used.

Adjacent boomerang-shaped segments in an annular element may be interconnected via a link extending from the top of a segment to the bottom of an adjacent segment. The links may range in design from a short, straight connector to any of the shapes described below for the interconnecting elements.

BRIEF DESCRIPTION OF THE FIGURES

FIG. 4 is a flat plan view of an embodiment of a stent configuration of the invention in the unexpanded condition;

DETAILED DESCRIPTION OF THE PREFERRED EMBODIMENTS

Figure 1:
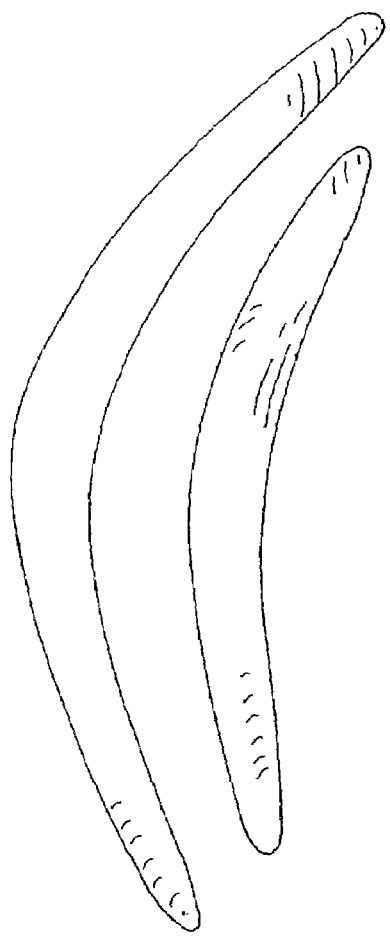
FIG. 1 is a schematic showing boomerang shapes.

For the purposes of this invention, the term boomerang is used to describe the shape of certain stent segments and is used in the sense as described in the *Websters New Collegiate Dictionary* with reference to FIG. 1 hereof:

"boomerang 1: A bent or angular throwing club which can be thrown so as to return near the starting point."

Figure 2:
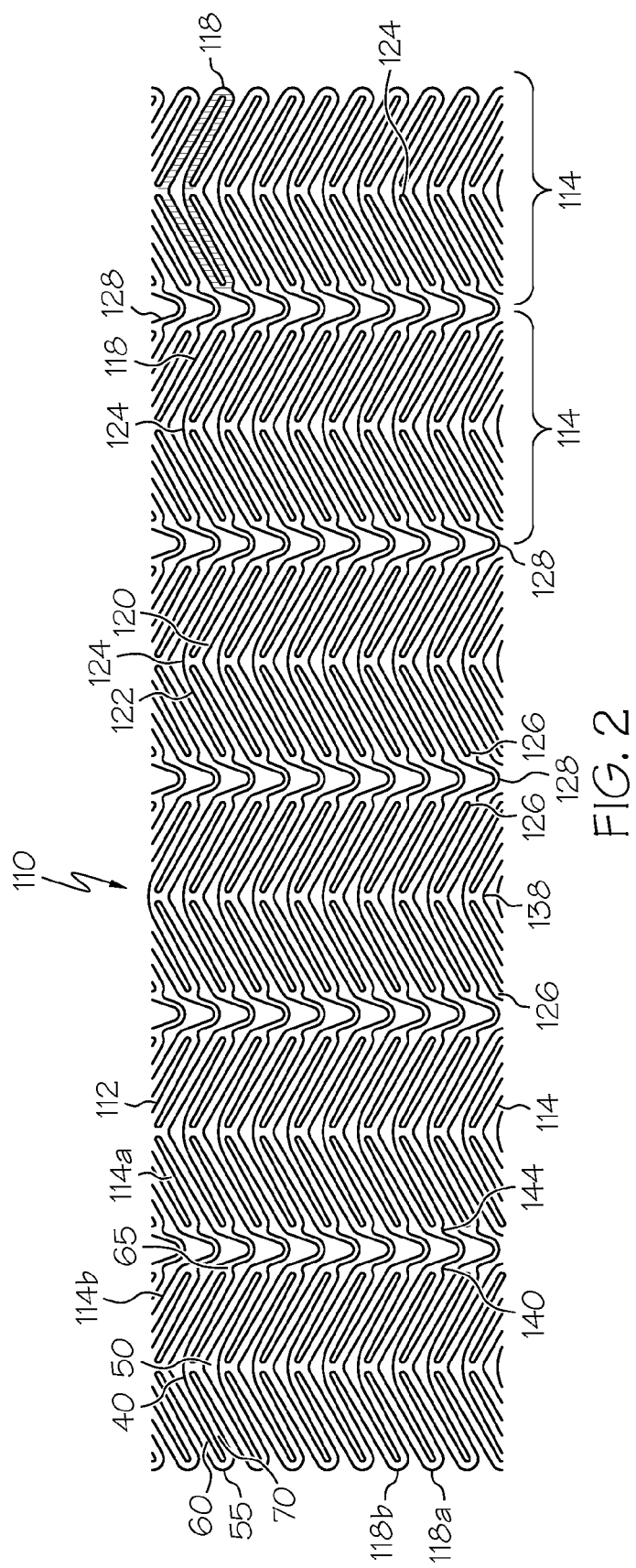
FIG. 2 is a flat plan view of an embodiment of a stent configuration of the invention in the unexpanded condition.

An embodiment of a generally cylindrical stent according to the invention is illustrated in the flat at 110 in FIG. 2 or FIG. 4. The stent may be formed of a metal tube such as nitinol, or stainless steel preferably, which has been etched or preferably laser cut to the configuration shown in the flat plan view of FIG. 2 or 4. The configuration may be formed in flat sheet and rolled into a cylinder with a welded seam or the like joining together edges 112 and 114, or the configuration may be formed directly in a small tube such as a hypotube. A tubular form of the stent is shown generally at 210 in FIG. 3.

Figure 3:
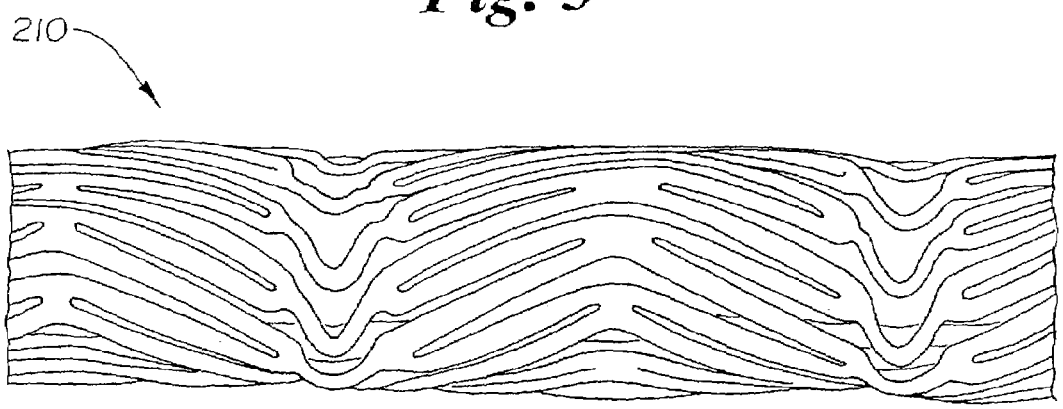
FIG. 3 is a longitudinal view of the stent of FIG. 2 in its normal tubular unexpanded condition.
Figure 6:
FIG. 6 is an interconnecting element that may be used to join adjacent annular elements in another embodiment of the invention.

The configurations shown in FIGS. 2-4 are made up of a plurality of aligned annular elements 114 aligned as shown to provide a generally cylindrical stent body. Each annular element 114 is comprised of a series of generally boomerang shaped segments indicated at 118 (see darkened segment in the Figures for clarity) having an open structure joined top 120 to bottom 122 at segment junction 124. Segments 118 are arranged or networked as shown in the Figures with ends 126 of neighboring segments on adjacent annular elements joined by interconnecting elements 128. In FIGS. 2-4, interconnecting element 128 is a U-shaped element which is a partly open curve. Alternative interconnecting elements including zig-zag shaped element 228 as shown in FIG. 6, which may be used in place of U-shaped element 128 to join adjacent annular elements 114 together.

The configurations of FIGS. 2 and 4 are substantially similar to one another, differing principally in the presence of a dimple 130 in each bottom 122 of each segment 118 in the configuration of FIG. 4. Without being bound by a particular theory, it is believed that the presence of the dimple limits the extent to which the stent buckles out of the plane on expansion.

It is desirable that the boomerang-shaped segments be at least substantially symmetric about a midline 138 extending from the top 120 of the segment to the bottom 122 of the segment. Midline 138 is situated midway between ends 126 of the segment.

Figure 5:
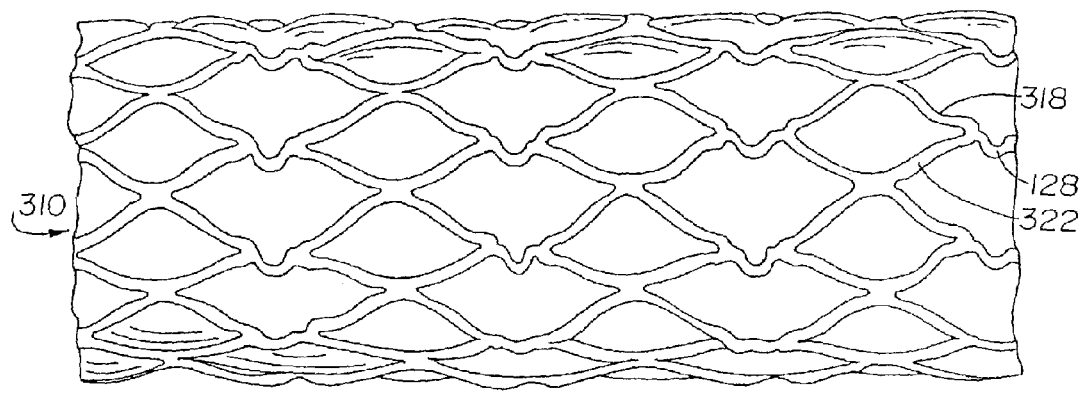
FIG. 5 is a longitudinal view of the stent of FIG. 3 in its tubular, expanded condition.

When the stent of FIG. 2 is expanded, as shown generally at 310 in FIG. 5 on a balloon for example, the boomerang-shaped segments 118 of the unexpanded stent take on a new configuration. The segments 318 take on the shape of rounded triangles with bulging bottoms 322.

It is desirable that the interconnecting elements be U-shaped as shown in FIGS. 2 and 4 or zig-zag shaped as shown in FIG. 6. However, in a more general sense, the invention contemplates the use of curvilinear as well as rectilinear interconnecting elements, including straight elements. Examples of other suitable connectors are disclosed in U.S. patent application Ser. No. 09/111,531 filed Jul. 8, 1998, U.S. patent application Ser. No. 08/846,164 filed Apr. 25, 1997, WO 97/32543 to Divysio Solutions LTD. and WO 97/40780 to David G. Jang, all of which are incorporated herein by reference. Of course, adjacent boomerang-shaped segments may also be joined side-by-side with a region of overlap between adjacent boomerang-shaped segments.

Figure 7:
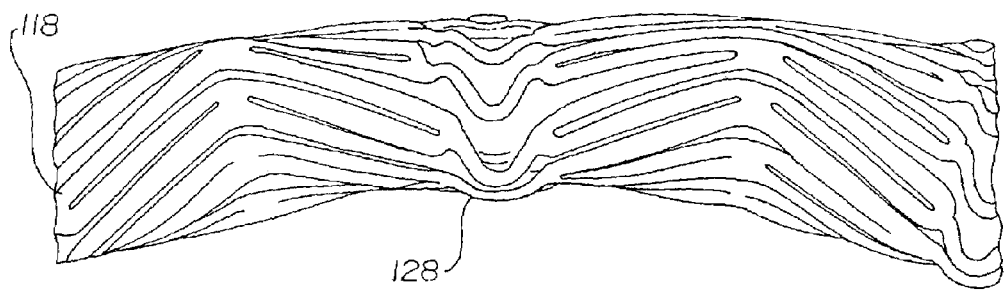
FIG. 7 is a view of the stent of FIG. 3 after being bent.

It is also desirable that interconnecting elements be flexible so as to accommodate bending of the stent without substantial distortion of the boomerang-shaped segments. FIG. 7 shows the stent of FIG. 3 having been bent. As shown in FIG. 7, as the stent is bent, interconnecting elements in tension open while interconnecting elements in compression close to accommodate bending of the stent.

Although as shown in the Figures an interconnecting element extends from each boomerang-shaped segment in an annular element to a nearest neighboring boomerang-shaped segment in an adjacent annular element, the invention further contemplates the possibility of an interconnecting element extending from each boomerang-shaped segment in an annular element to a next-nearest neighboring boomerang-shaped segment in an adjacent annular element. In the latter case, the first end 140 and second end 144 of each interconnecting element 128 would be circumferentially offset along the stent.

In a more general sense, the invention further contemplates a stent in which each adjacent annular element is interconnected by one or more interconnecting elements and each interconnecting element extends from an end of a boomerang-shaped segment in one annular element to an end of a boomerang-shaped segment in an adjacent annular element. As such, an interconnecting element need not extend from each boomerang-shaped segment. An example of this is a stent in which interconnecting elements extend from every second or third boomerang-shaped segment in an annular element.

The invention also contemplates the possibility of altering the orientation of some of the annular elements. In one such embodiment, adjacent annular elements in the flat pattern are rotated by 180° relative to one another so that adjacent annular elements point in opposite directions.

Figure 12:
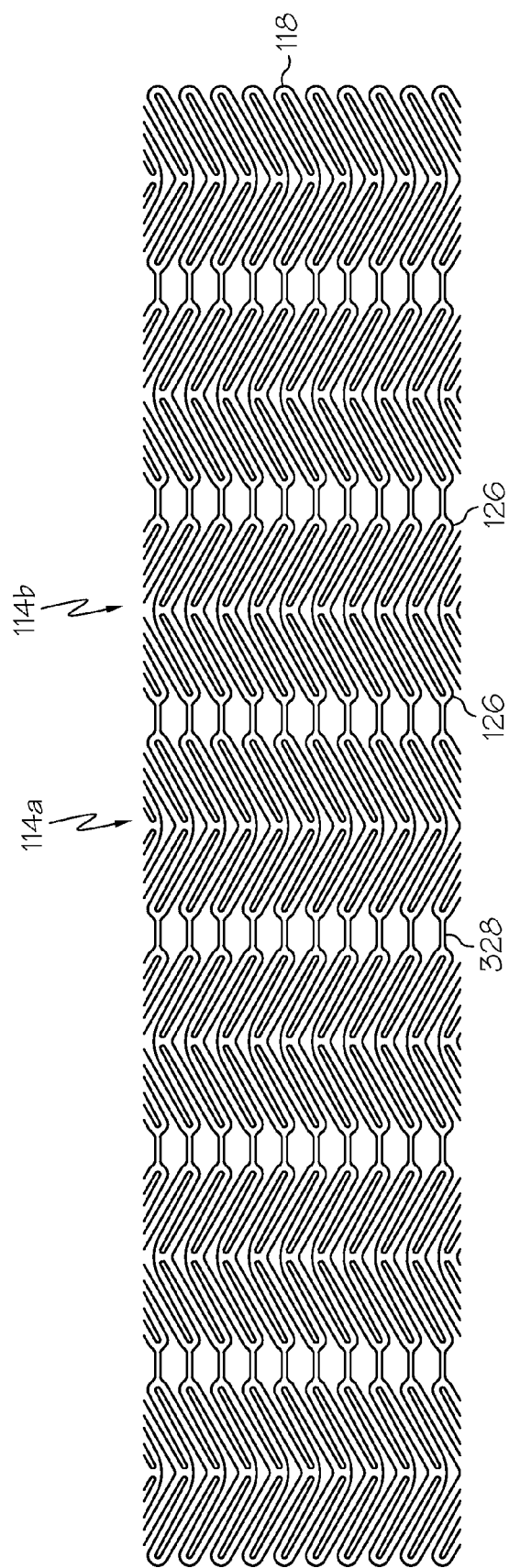
FIG. 12 shows a flat view of an alternate unexpanded stent configuration according to the invention.

For example, FIG. 12 shows annular elements 114a, 114b having an antiparallel chevron pattern. FIG. 12 also shows longitudinally straight connectors 328.

Although the ends of nearest neighboring segments in adjacent annular elements are shown in the figures as aligned with one another along the circumference of the stent, the invention further contemplates embodiments of the stent in which nearest neighboring segments in adjacent annular elements are circumferentially displaced relative to one another.

In yet another series of embodiments, adjacent (or non-adjacent) annular elements may be formed of different sized boomerang-shaped elements. As such, adjacent (or non-adjacent) annular elements may span different lengths. Alternatively, adjacent (or non-adjacent) annular elements may comprise different numbers of boomerang-shaped segments.

Figure 8:
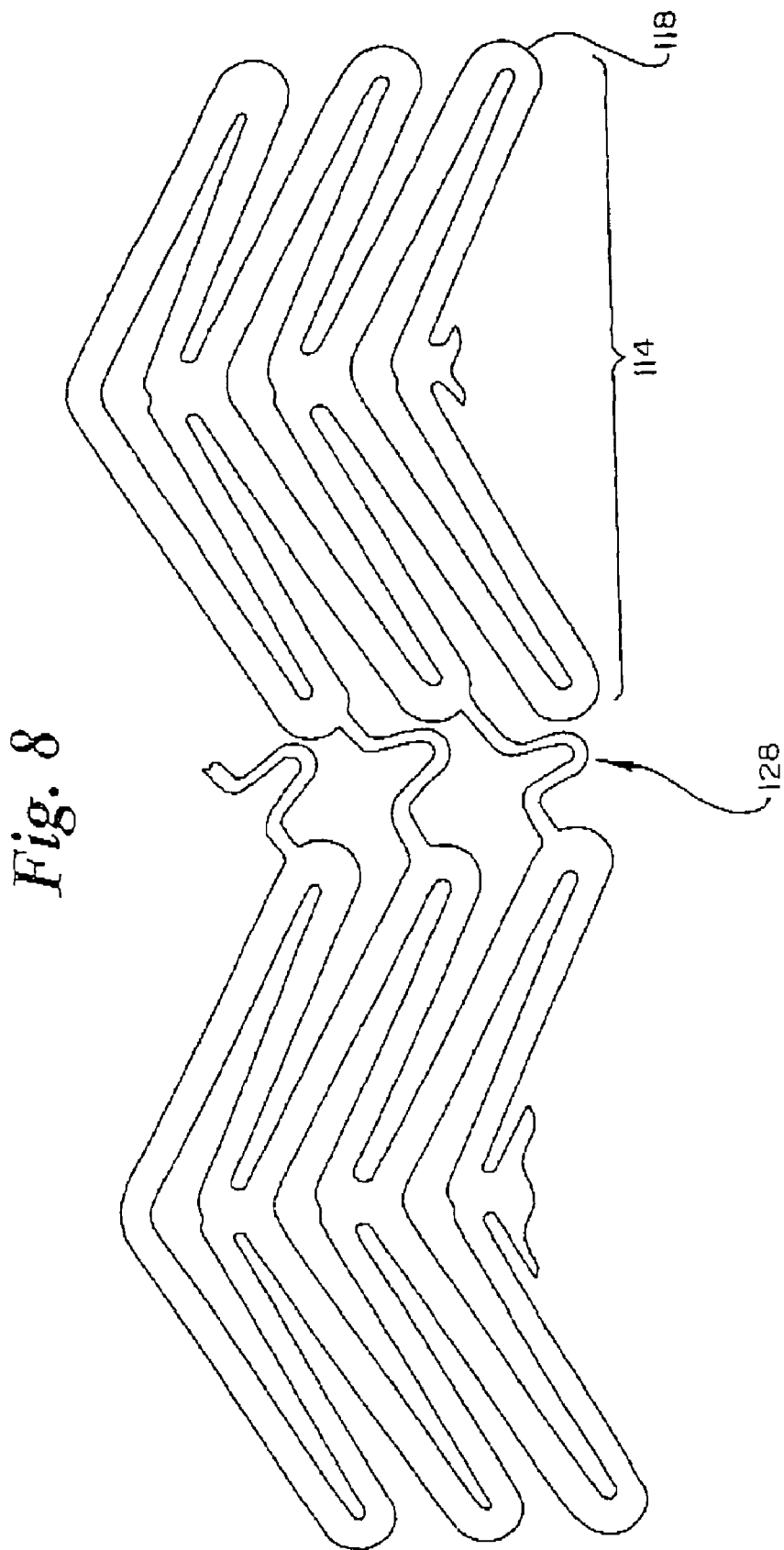
FIG. 8 is a portion of an enlarged flat plan view of an embodiment of the invention in the unexpanded condition.

FIG. 8 illustrates a portion of the configuration of an embodiment of the invention. The embodiment is made of a plurality of aligned annular elements 114. Each annular element 114 is comprised of generally boomerang shaped segments 118. The segments 118 of each annular element 114 are connected via connectors 128. As shown in the embodiment the ends of the connectors are circumferentially displaced from each other.

Figure 9:
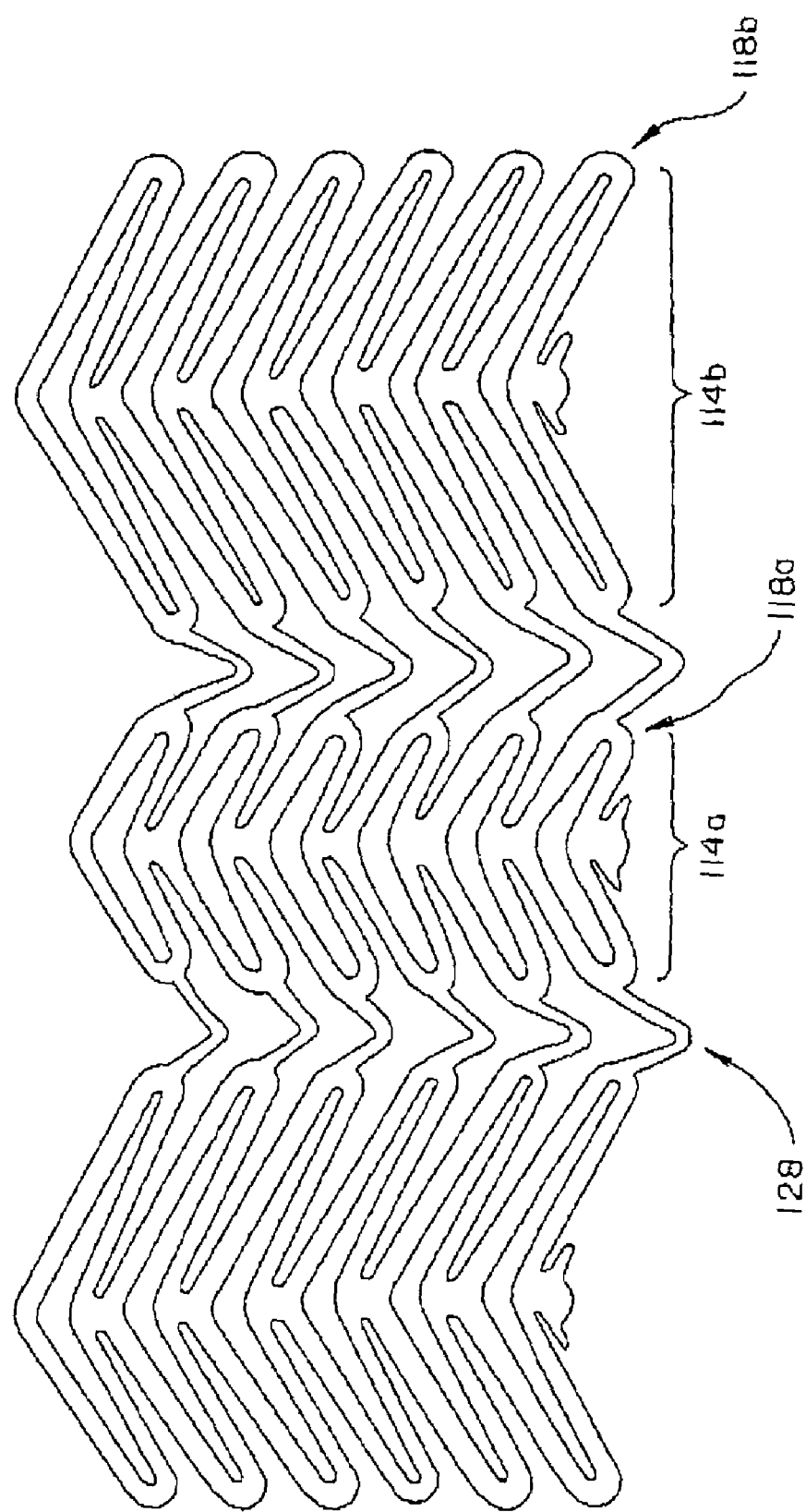
FIG. 9 is a portion of an enlarged flat plan view of an embodiment of the invention in the unexpanded condition.

FIG. 9 illustrates a portion of the configuration of an embodiment of the invention. The embodiment is made of a plurality of aligned annular elements 114. Each annular element 114 is comprised of generally boomerang shaped segments 118. The segments 118 of each annular element 114 are connected via connectors 128. Aligned annular elements 114a and 114b are of different lengths.

Figure 10:
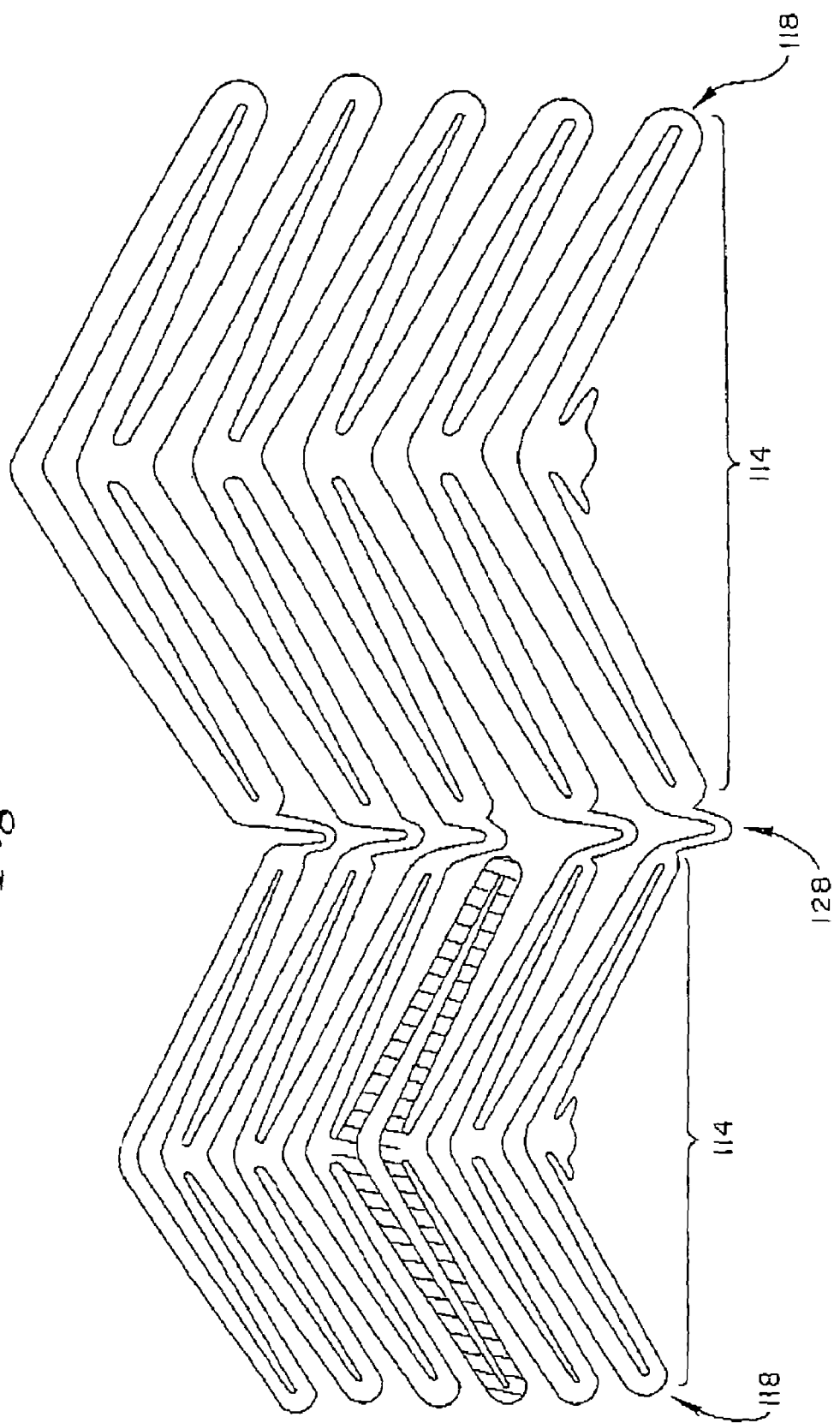
FIG. 10 is a portion of an enlarged flat plan view of an embodiment of the invention in the unexpanded condition.

FIG. 10 illustrates a portion of the configuration of an embodiment of the invention. The embodiment is made of a plurality of aligned annular elements 114. Each annular element 114 is comprised of generally boomerang shaped segments 118. Segments 118 of each annular element 114 are connected via connectors 128. The stent has a first band with a first number of first cells and another first band having a second number of first cells different from the first number.

Figure 11:
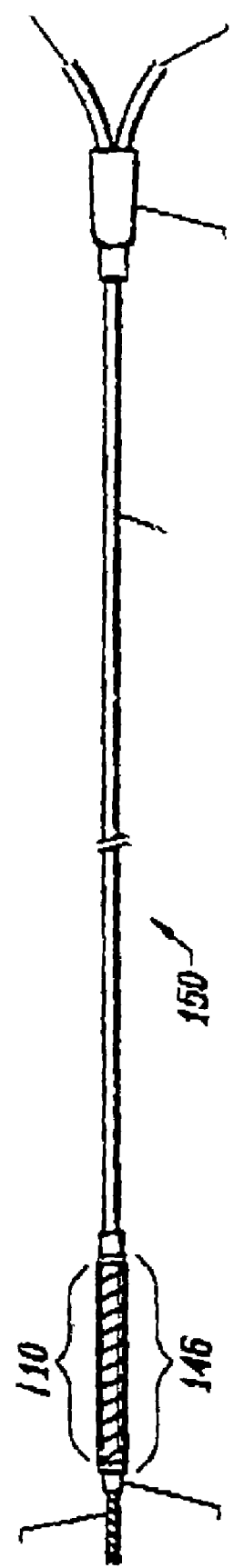
FIG. 11 shows a delivery balloon catheter.

FIG. 11 shows a delivery balloon catheter generally at 150 with stent 110 disposed about balloon 146.

Although in the embodiment of FIGS. 2-4, segment junction 124 is shown as a small, straight link extending from the top of one segment to the bottom of an adjacent segment, the invention also contemplates the possibility of adjacent boomerang-shaped segments within an annular element being connected by U shaped links, zig-zag shaped links or any of the shapes disclosed above for the interconnecting elements. Additionally, other shaped segments may be interspersed among the boomerang-shaped segments.

Referring again to FIG. 2, in some embodiments, each annular element 114 can be described as a ring 114 that extends around a circumference of the stent. The boomerang-shaped segments 118 can be described as closed members 118. In some embodiments, a closed member 118 defines a v-shaped opening 50. In some embodiments, a closed member 118 comprises a longer strut 60 and a shorter strut 70 connecting curved peak 55 and valley 65 segments. Each strut 60, 70 can further comprise a curved portion 40 curved substantially symmetrically about a circumference of the stent, such as a circumferential midline 138 of a ring 114.

In some embodiments, the closed members 118 within a ring 114 form a nested chevron pattern. In some embodiments, the struts 60, 70 of the closed members 118 within a ring 114 form a nested chevron pattern. In some embodiments, the dosed members 118 and/or the struts 60, 70 of a first ring 114a and a second ring 114b form a parallel chevron pattern relative to one another.

In some embodiments, the shorter strut 70 of a closed member 118 is oriented within a nest defined by the longer strut 60 of the closed member 118. In some embodiments, the longer strut 60 of a first closed member 118a is oriented within a nest defined by the shorter strut 70 of an adjacent closed member 118b.

In some embodiments, adjacent closed members 118 within a ring 114 are connected by a junction 124. In some embodiments, the junctions 124 of a ring 114 are aligned along a circumferential midline 138 of the ring 114.

In some embodiments, the peak segments 55 of one ring 114a are longitudinally aligned with valley segments 65 of another ring 114b. In some embodiments, the peak segments 55 of one ring 114a are longitudinally aligned with peak segments 55 of another ring 114b.

The inventive stent may be self-expanding or mechanically expandable such as by balloon. The stent may be made of a variety of suitable bio-compatible materials including metal, plastic and any other material capable of functioning as an expandable stent. For example, the stent may be of metal wire or ribbon such as tantalum, stainless steel or the like or of metal sheeting or metal tubing. It may be thin-walled. It may be of shape memory alloy such as Nitinol or the like.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical device comprising:
    a catheter and a radially expandable stent mounted on the catheter, the stent comprising a hollow, cylindrical body comprising first and second rings extending circumferentially around the cylindrical body, the first and second rings each comprising a plurality of closed members, each closed member comprising a longer strut and a shorter strut connecting curved peak and valley segments, the longer and shorter struts each comprising a curved portion curved substantially symmetrically about a single circumference of the stent such that the closed members within a ring form a nested chevron pattern;
    circumferential connectors between the longer strut and the shorter strut of circumferentially adjacent closed members; and
    at least one longitudinal connection between the first and second rings.

2. The medical device of claim 1 wherein the closed members further comprises an indentation positioned on the shorter strut, such that the indentation is substantially circumferentially aligned with the circumferential connector attached to the shorter strut.

3. The medical device of claim 1 wherein the first and second rings are arranged in a parallel chevron pattern relative to each other.

4. The medical device of claim 1 wherein the first and second rings are arranged in an antiparallel chevron pattern relative to each other.

5. The medical device of claim 1 wherein the peaks of the first ring are longitudinally aligned with the valleys of the second ring.

6. The medical device of claim 1 wherein the peaks of the first ring are not longitudinally aligned with the valleys of the second ring.

7. The medical device of claim 1 wherein the peaks of the first ring are longitudinally aligned with the peaks of the second ring.

8. The medical device of claim 1 wherein at least one longitudinal connection is formed by a longitudinal connector.

9. The medical device of claim 8 wherein the longitudinal connector is curved.

10. The medical device of claim 8 wherein the longitudinal connector is straight.

11. The medical device of claim 1 further comprising at least one radiopaque marker.

12. The medical device of claim 1 wherein the radially expandable stent is a balloon-expandable stent.

13. The medical device of claim 1 wherein the radially expandable stent is a self-expanding stent.

14. A stent comprising:
    a plurality of interconnected rings, each ring extending around a circumference of the stent, each ring comprising a plurality of closed members, each closed member defining a V-shaped opening, each V-shaped opening being symmetric across a midline that comprises a stent circumference, each closed member comprising a longer bent strut and a shorter bent strut, wherein the closed members within a ring form a nested chevron pattern.

15. The stent of claim 14, wherein the bent struts of the closed members within a ring form a nested chevron pattern.

16. The stent of claim 14, wherein the shorter strut of a closed member is oriented within a nest defined by the longer strut of the closed member.

17. The stent of claim 14, wherein the longer strut of a first closed member is oriented within a nest defined by the shorter strut of a second closed member.

18. The stent of claim 14, wherein each bent strut has a v-shape comprising first and second straight portions connected by a curved portion.

19. The stent of claim 14, wherein adjacent closed members within a ring are connected by a junction, the junctions of a ring being aligned along a circumferential midline of the ring.

* * * * *